United States Patent [19]

Bellows et al.

[11] Patent Number: 5,210,333
[45] Date of Patent: May 11, 1993

[54] BENZENE REMOVAL FROM HYDROCARBON STREAMS

[75] Inventors: Richard J. Bellows, Hampton; Gary B. McVicker; Joseph E. Baumgartner, both of Califon; James P. Dennis, Chatham, all of N.J.

[73] Assignee: Exxon Research and Engineering Company, Florham Park, N.J.

[21] Appl. No.: 953,372

[22] Filed: Sep. 30, 1992

[51] Int. Cl.$^5$ .................. C07C 7/12; C07C 7/152; C07C 5/00; C10G 25/00
[52] U.S. Cl. .................... 585/827; 585/826; 585/831; 585/850; 585/841; 585/264; 585/269; 208/310 Z
[58] Field of Search ............ 585/827, 826, 831, 850, 585/841, 264, 269; 208/310 Z

[56] References Cited

U.S. PATENT DOCUMENTS 3,265,755 8/1966 Evans et al. .................. 585/827

FOREIGN PATENT DOCUMENTS 55-98123 7/1980 Japan.

Primary Examiner—Anthony Mc Farlane
Assistant Examiner—Nhat D. Phan
Attorney, Agent, or Firm—Jay Simon

[57] ABSTRACT

A method for the separation of benzene from a hydrocarbon stream, such as a gasoline boiling range stream, which comprises contacting the hydrocarbon stream with an adsorbent capable of selectively adsorbing the benzene from the stream, hydrogenating the adsorbed benzene to cyclohexane, and desorbing the cyclohexane from the adsorbent. The hydrogenation of the benzene to cyclohexane facilitates the removal of the benzene from the adsorbent.

15 Claims, No Drawings

BENZENE REMOVAL FROM HYDROCARBON STREAMS

FIELD OF THE INVENTION

This invention relates to a method for the removal of benzene from hydrocarbon streams, particularly gasoline boiling range streams, using adsorption and desorption techniques.

BACKGROUND OF THE INVENTION

Motor gasolines are undergoing ever changing formulations in order to reduce the level of potentially environmentally damaging components and to meet new government legislation. One requirement is the reduction of benzene in gasoline down to very low levels, for example less than one percent. Other applications may involve removing benzene from a variety of blending, product, or effluent waste streams.

In conventional refining processes producing gasoline streams, the resulting stream typically contains 2-3 percent benzene. While various techniques can be used to selectively remove this benzene, the use of solid adsorbents, such as molecular sieves, presents advantages over other techniques such as distillation and solvent extraction. Distillation is not suitable primarily because benzene forms low boiling azeotropes with normal hexane and naphthenes such as methyl cyclopentane and cyclohexane. Alternatively, extraction of the benzene with a solvent, such as sulfolane, is technically feasible but presents some disadvantages including the use of special equipment to compensate for the corrosive nature of the sulfolane.

It is often the desorption step that presents difficulties in adsorption based separation processes. The extent to which a desorbent will displace an adsorbed material depends upon the relative strength of adsorption of the desorbent over the adsorbed material. Desorption of aromatics from solid adsorbents such as zeolites is particularly difficult as aromatic molecules tend to be very strongly adsorbed relative to paraffinic, naphthenic and olefinic molecules. Thus adsorbed aromatics, such as benzene, are usually desorbed using a large excess of desorbent such as toluene or xylene. Even so, toluene and xylene often do not readily displace benzene leading to long desorption times.

U.S. Pat. Nos. 3,207,803 and 3,243,470 disclose a process for the selective removal of straight-chain, olefinic hydrocarbons from an admixture with branched and cyclic hydrocarbons by adsorbing the unsaturated hydrocarbons onto a modified zeolite. Hydrogen is introduced, either simultaneously with the feed or following the feed, to hydrogenate the adsorbed unsaturated hydrocarbons to more saturated hydrocarbons in order, it is stated, to facilitate their removal from the zeolite. These patents neither mention nor suggest the advantages of first hydrogenating adsorbed aromatic compounds to facilitate their desorption.

Recently filed U.S. patent application Ser. No. 729,679, filed Jul. 15, 1992, relates to selective removal of benzene from process streams but does not mention conversion of the benzene to cyclohexane.

SUMMARY OF THE INVENTION

The present invention relates to an improved process for the adsorption/desorption of benzene from a wide range of processing streams.

Accordingly, the invention provides, in one aspect, a method of substantially removing adsorbed benzene from an adsorbent which comprises converting the adsorbed benzene to cyclohexane, and desorbing the cyclohexane from the adsorbent. Desorption may be accomplished with a variety of convenient desorbents. In particular, benzene in the fresh feed in the subsequent adsorption cycle is a convenient desorbent and eliminates the need for separate desorbent inventories and handling.

With some benzene containing streams, it is possible that certain heavy aromatic or polar compounds may compete with benzene during adsorption cycles and may be difficult to desorb. For example, naphthalene is mentioned in U.S. patent application Ser. No. 729,678, filed Jul. 15, 1991, to Kaul et al. Hydrogenation will convert most heavy aromatics and polar compound into more weakly adsorbed compounds, which may be easily desorbed by subsequent typical desorbents, such as benzene and toluene. The ability of a hydrogenation step to convert these compounds prevents them from accumulating and poisoning the adsorbent over repeated adsorption/desorption cycles.

In a second aspect, the invention provides a method for the essentially complete separation of benzene from a feed mixture comprising benzene and at least one other hydrocarbon, which method comprises contacting the feed mixture with an adsorbent capable of selectively adsorbing benzene from the feed mixture, converting the adsorbed benzene to cyclohexane, and desorbing the cyclohexane from the adsorbent. Benzene in the fresh feed of the subsequent adsorption cycle is one convenient desorbent.

The invention has the advantage that it greatly facilitates the removal of benzene from the adsorbent. Cyclohexane is less strongly adsorbed than benzene, and therefore, the conversion of the adsorbed benzene to cyclohexane prior to desorption, enables the adsorbed material to be more readily displaced using conventional desorbents by simply using fresh feed. After desorption, the cyclohexane may be reconverted to benzene, using conventional dehydrogenation techniques, if desired. In many cases, cyclohexane is more environmentally acceptable than benzene.

The invention is especially applicable to the production of reduced-benzene gasolines as it provides a method for removing benzene, which method can be conveniently applied to gasoline process streams. This invention is also generally applicable for removal of benzene from process streams containing trace as well as large quantities of benzene.

DETAILED DESCRIPTION OF THE INVENTION

The present invention provides a method for the removal of benzene from a wide variety of hydrocarbon containing mixtures, and in particular is directed towards facilitating the desorption of benzene after it has been adsorbed onto an adsorbent.

The feed mixture may be any mixture containing benzene and at least one other hydrocarbon. Generally, the feed mixture will be a refinery process stream, for example a reformate, hydrocrackate, light naphtha or sulfolane raffinate, or it may be a blend stream or a specialty chemical stream. Advantageously the feed mixture is a process stream boiling in the gasoline boiling range of about 25° C. to about 400° C., or a heartcut fraction of a gasoline process stream. The feed may be in either the vapor or liquid phase, but is more usually in the vapor phase. The types of hydrocarbons present in these streams may include paraffins, naphthas, aromatics, olefins, polar compounds, oxygenates and other heteroatom-containing hydrocarbons. The amount of benzene contained in a refinery process stream can vary, but is typically about 1 ppm to 30 wt %; higher for heartcut fractions.

To remove the benzene from the feed mixture, the feed is contacted with an adsorbent. Typically, the feed is fed into an adsorption zone which contains a solid adsorbent capable of selectively adsorbing benzene from the stream. The adsorption zone (which may also act as the desorption zone) may be run under any suitable mode, for example fixed bed, simulated moving bed or magnetically stabilized bed. The operating conditions in the adsorption zone may be any suitable conditions, the temperature being, for example, from subambient to about 400° C., preferably from 25° C. to 200° C.; and the pressure being, for example, from about 0.01 atm to about 10 atm, preferably from 0.1 atm to 10 atm. The adsorption zone may comprise only one vessel, or may comprise two or more vessels with, for example the appropriate plumbing for continuous adsorption and regeneration of the adsorbent.

The adsorbent may be any adsorbent capable of selectively adsorbing benzene from the other components of the feed mixture under the adsorption conditions. Preferred adsorbents are zeolites, for example cation exchanged zeolites such as X and Y zeolites; Beta zeolites, L zeolites, mordenites or other 10 to 12 ring zeolites. The cation is selected from alkali metals, alkaline earth metals and rare earth metals, for example Li, Na, K, Cs, Rb or a mixture thereof. Preferably the zeolite adsorbents have a silicon to aluminum ratio of less than 20, more preferably from 1 to 3, and an average pore diameter of from about 5 Å to about 9 Å, more preferably from about 6 Å to about 8 Å. Particularly preferred adsorbents are NaX and NaY zeolites, especially those that are at least partially dehydrated. They can be dehydrated by calcining at a temperature from about 95° C. to about 260° C. for about 1 to about 4 hours.

The product stream leaving the adsorption zone is substantially benzene-free, and is suitable for use in applications requiring process streams with minimal benzene content, for example reduced-benzene or benzene-free gasolines.

A preferred process for the adsorption of benzene from hydrocarbon feed mixture is given in the above mentioned U.S. patent application Ser. No. 729,678, the disclosures of which are incorporated herein by reference.

Following the adsorption step, the adsorbed benzene must be removed from the adsorbent in order to recover the benzene, if desired, and to regenerate the adsorbent.

This removal is facilitated if the benzene is first converted to cyclohexane and then the cyclohexane desorbed using a suitable desorbent.

The benzene can be converted to cyclohexane using conventional hydrogenation techniques, and this may be carried out in situ in the adsorption/desorption zone. Thus, to hydrogenate the benzene, a hydrogen stream is fed into the adsorption zone which reacts with the benzene in the presence of a hydrogen activation catalyst. The hydrogen stream may be obtained from any suitable source, for example pure hydrogen, hydrogen exiting from a reformer process or hydrogen obtained as a by-product from another refinery or chemical process. The hydrogen stream may be 100% hydrogen or may be diluted with another gas, for example light alkanes, carbon dioxide or an inert gas. Preferably the stream contains 5 to 100 vol %, more preferably 30 to 100 vol % hydrogen, and is typically fed into the adsorption/desorption zone at a pressure of 1 to 30 atm.

Hydrogenation activation catalysts are well known and typically comprise 0.05 to 10 wt %, preferably 0.1 to 2 wt % of a metal such as platinum, palladium, ruthenium, rhodium, iridium, nickel or copper carried on a support. Advantageously the support is the zeolite of the adsorbent, either as the sole support or admixed with another support material such as a silica, alumina, titania or silica-alumina (including clays).

The hydrogenation is typically carried out at temperatures of 0°–300° C., preferably 25°–200° C.; time 4 seconds to 4 hours, preferably 10–60 minutes; pressure 0.1–30 atm, preferably 1–10 atm. Under these conditions generally about 50% to 100%, preferably 90% to 100%, of the benzene is converted to cyclohexane.

After hydrogenation, the cyclohexane can then be displaced from the zeolite adsorbent using any suitable desorbent, usually a liquid hydrocarbon, preferably an aromatic such as toluene, xylene, benzene or ethylbenzene; or a $C_6$ or higher paraffin, olefin or naphtha; or a hydrocarbon stream containing $C_6$ or higher aromatic or aliphatic compounds.

More preferably, the desorbent is the benzene-containing hydrocarbon feed mixture, i.e. the feed mixture from which the benzene is to be removed. The process can therefore be continuous, the cyclohexane desorption step of one feed cycle being the benzene adsorption step of the next feed cycle. Thus, in a preferred aspect, the invention provides a quasi-continuous process for the substantial separation of benzene from a feed mixture comprising benzene and at least one other hydrocarbon, which process comprises (i) contacting the feed mixture with an adsorbent capable of selectively adsorbing benzene from the feed mixture, (ii) converting the adsorbed benzene to cyclohexane, and (iii) desorbing the cyclohexane from the adsorbent using the said mixture, the benzene in the feed mixture displacing the cyclohexane from the adsorbent (and other aromatics).

Alternatively the cyclohexane may be desorbed using other desorbing techniques, for example temperature or pressure swing or using these in combination with a desorbent.

The desorbed cyclohexane may be used in any desired manner. For example, if it is desorbed using the benzene-containing feed mixture, it may simply be left in the mixture, thus forming part of the separated feed, e.g. a gasoline process stream. Alternatively the cyclohexane may be recovered, for use for example in chemical processing, by desorbing the cyclohexane from the adsorbent, for example with toluene or xylene, as a displacement stream and then separating the cyclohexane from the toluene or xylene using an appropriate separation technique, for example distillation.

The recovered cyclohexane may, if desired, be reconverted to benzene by dehydrogenation.

The invention shall now be illustrated by the following non-limiting Examples.

EXAMPLES

The following two Examples clearly demonstrate the fundamental steps of adsorption of benzene followed by conversion of the adsorbed benzene to cyclohexane followed by desorption of the cyclohexane with further benzene.

EXAMPLE 1

This Example used a recirculating batch reactor system containing, as hydrogen activation catalyst, 0.8 wt % Pt supported on a Na(K)X zeolite, i.e., an X zeolite exchanged with a mixture of Na and K cations. The zeolite also acted as the benzene adsorbent. The catalyst had been dried and calcined at 350° C. The reactor was pretreated with hydrogen at 350° C. for 2 hours, cooled to room temperature, and flushed with helium.

Benzene was then introduced into the reactor to an amount of 3.5 mmoles/g catalyst, and mixed with helium to reach a total pressure of 800 torr. This mix was passed through the catalyst/adsorbent bed at room temperature for 18 minutes. The amount of benzene adsorbed was determined by gas chromatographic (GC) analysis taken after 4 and 18 minutes, and showed that the benzene adsorption equilibrated rapidly and that a total of 1.9 mmoles/g catalyst of benzene had been adsorbed onto the zeolite adsorbent.

The system was then evacuated and filled with pure hydrogen to a pressure of 798 torr. The catalyst was heated to 100° C. and the hydrogen flow maintained for 330 minutes. GC analysis indicated that a portion of adsorbed benzene was converted to cyclohexane.

The system was evacuated again and the cyclohexane displaced from the adsorbent by introducing into the reactor 2.6 mmoles/g catalyst of benzene mixed with helium to a total pressure of 806 torr. This mix was passed through the catalyst for 35 minutes at room temperature. GC analysis showed that a total amount of cyclohexane desorbed was 2.0 mmoles/g catalyst and the total amount of benzene readsorbed was 1.7 mmoles/g catalyst. This data demonstrates that hydrogenation converted essentially all of the adsorbed benzene into cyclohexane which was then desorbed by the subsequent benzene adsorption. Minor differences in the moles sorbed and desorbed merely shows the experimental limits of the apparatus and GC sampling.

EXAMPLE 2

Example 1 was repeated except that the hydrogen activation catalyst/adsorbent employed was an admix of 0.04 g 10% Ru/SiO$_2$ and 0.30 g Na(K)X zeolite.

The following alterations were made to the process conditions:

Benzene adsorption: The amount of benzene introduced was 4.3 mmole/g catalyst mixed with helium to a total pressure of 796 torr. The mix was passed through the catalyst for 22 minutes.

Hydrogenation to cyclohexane: Hydrogenation was carried out at room temperature for 55 minutes using pure hydrogen at a pressure of 794 torr.

Cyclohexane desorption/benzene readsorption: The amount of benzene introduced was 4.3 mmoles/g catalyst mixed with helium to a total pressure of 803 torr. The mix was passed through the catalyst for 33 minutes.

GC analysis at the various stages showed that 2.07 mmoles/g catalyst of benzene was adsorbed during the initial adsorption stage; essentially 100% of the adsorbed benzene was converted to cyclohexane; and 2.13 mmoles/g catalyst of cyclohexane was desorbed and 1.97 mmole/g catalyst of benzene was readsorbed.

What is claimed is:

1. A method of substantially removing adsorbed benzene from an adsorbent which comprises converting the adsorbed benzene to cyclohexane, and desorbing the cyclohexane from the adsorbent.

2. The method of claim 1 wherein the adsorbent has an average pore diameter greater than the size of a benzene molecule.

3. The method of claim 1 wherein the benzene is converted to cyclohexane by catalytic hydrogenation.

4. The method of claim 1 wherein the cyclohexane is desorbed using a hydrocarbon desorbent.

5. The method of claim 4 wherein the hydrocarbon desorbent is an aromatic compound selected from benzene, toluene, xylene, ethyl benzene or a mixture thereof.

6. The method of claim 1 wherein the cyclohexane desorbed from the adsorbent is reconverted to benzene.

7. A method for the substantial separation of benzene from a feed mixture comprising benzene and at least one other hydrocarbon, which method comprises contacting the feed mixture with an adsorbent capable of selectively adsorbing benzene from the feed mixture, converting the adsorbed benzene to cyclohexane, and desorbing the cyclohexane from the adsorbent.

8. The method of claim 7 wherein the feed mixture is a refinery process stream boiling in the gasoline boiling range.

9. The method of claim 7 wherein the adsorbent is a zeolite.

10. The method of claim 9 wherein the adsorbent is a cationic exchanged L, X, Y, or mordenite type zeolite, the cation being selected from alkali metals, alkaline earth metals and rare earth metals.

11. The method of claim 7 wherein the benzene is converted to cyclohexane by hydrogenation in the presence of a hydrogen activation catalyst, the catalyst being supported by the adsorbent either as the sole support material or admixed with another support material.

12. The method of claim 11 wherein the hydrogen activation catalyst is supported platinum.

13. The method of claim 7 wherein the benzene adsorption, conversion to cyclohexane, and cyclohexane desorption are conducted in the same reactor vessel.

14. The method of claim 7 wherein the desorbent is the feed mixture.

15. A continuous process for the substantial separation of benzene from a feed mixture comprising benzene and at least one other hydrocarbon, which process comprises:
  (i) contacting the feed mixture with an adsorbent capable of selectively adsorbing benzene from the feed mixture;
  (ii) converting the adsorbed benzene to cyclohexane; and
  (iii) desorbing the cyclohexane from the adsorbent using as desorbent the feed mixture, the benzene in the feed mixture displacing the cyclohexane from the adsorbent.

* * * * *